US008501439B2

(12) United States Patent
Rattenholl et al.

(10) Patent No.: US 8,501,439 B2
(45) Date of Patent: Aug. 6, 2013

(54) METHOD FOR OBTAINING ACTIVE PRO-NGF AND BETA-NGF

(75) Inventors: Anke Rattenholl, Halle (DE); Adelbert Grossmann, Eglfing (DE); Elisabeth Schwarz, Halle (DE); Rainer Rudolph, Halle (DE)

(73) Assignee: Scil Proteins GmbH, Halle (DE)

( * ) Notice: Subject to any disclaimer, the term of this patent is extended or adjusted under 35 U.S.C. 154(b) by 256 days.

(21) Appl. No.: 12/765,229

(22) Filed: Apr. 22, 2010

(65) Prior Publication Data

US 2010/0203589 A1 Aug. 12, 2010

Related U.S. Application Data

(62) Division of application No. 09/807,096, filed as application No. PCT/EP99/07613 on Oct. 11, 1999, now Pat. No. 8,318,671.

(30) Foreign Application Priority Data

Oct. 9, 1998 (EP) ..................................... 98119077

(51) Int. Cl.
C12N 15/18 (2006.01)

(52) U.S. Cl.
USPC ....................................................... 435/69.4

(58) Field of Classification Search
None
See application file for complete search history.

(56) References Cited

U.S. PATENT DOCUMENTS

| 5,169,762 | A | | 12/1992 | Gray et al. |
| 5,235,043 | A | * | 8/1993 | Collins et al. ................. 530/399 |
| 5,593,865 | A | | 1/1997 | Rudolph et al. |
| 5,606,031 | A | | 2/1997 | Lile et al. |
| 5,683,894 | A | | 11/1997 | Edwards et al. |

FOREIGN PATENT DOCUMENTS

| EP | 0 544 293 | | 6/1993 |
| EP | 0 786 520 A1 | | 7/1997 |
| JP | 06-327489 | | 11/1994 |
| JP | 07-265092 | | 10/1995 |
| JP | 09-023883 | * | 1/1997 |
| WO | WO95/30686 | | 11/1995 |
| WO | WO97/28272 | | 8/1997 |
| WO | WO97/47735 | | 12/1997 |
| WO | WO00/22119 | | 4/2000 |

OTHER PUBLICATIONS

Advisory Action corresponding to U.S. Appl. No. 09/807,096 dated Apr. 13, 2009.
Boutilier et al., "Proneurotrophins Require Endocytosis and Intracellular Proteolysis to Induce TrkA Activation," Journal of Biological Chemistry. vol. 283, No. 19 pp. 12709-12716 (2008).
Cong et al., "Protein Splicing Involving the *Saccharomyces cerevisiae* VMA Intein," The Journal of Biological Chemistry. vol. 271, No. 36 pp. 22159-22168 (1996).

English translation of Japanese Examination Report corresponding to Japanese Patent Application No. 2000-576009 dated Aug. 11, 2009.
International Search Report corresponding to International Application No. PCT/EP99/07613 dated Feb. 11, 2000.
Kliemannel et al., "The pro-peptide of proNGF: Structure formation and intramolecular association with NGF," Protein Science. vol. 16 pp. 411-419 (2007).
Kliemannel et al., "Examination of the Slow Unfolding of Pro-Nerve Growth Factor Argues against a Loop Threading Mechanism for Nerve Growth Factor," Biochemistry. vol. 45 pp. 3517-3524 (2006).
Marston, "The purification of eukaryotic polypeptides synthesized in *Escherichia coli*," Biochem. J., vol. 240 (1986).
Noel, J.P., and Tsai, M., Phospholipase A2 Engineering: Design, Synthesis, and Expression of a Gene for Bovine (Pro)Phospholipase A2. Journal of Cellular Biochemistry. vol. 40, No. 3 pp. 309-320 (1989).
Nykjaer et al., "Sortilin is essential for proNGF-induced neuronal cell death," Nature. vol. 427 pp. 843-848 (2004).
Official Action corresponding to U.S. Appl. No. 09/807,096 dated Sep. 18, 2006.
Official Action corresponding to U.S. Appl. No. 09/807,096 dated Feb. 19, 2008.
Official Action corresponding to U.S. Appl. No. 09/807,096 dated Oct. 8, 2008.
Official Action corresponding to U.S. Appl. No. 09/807,096 dated Jun. 17, 2009.
Official Action corresponding to U.S. Appl. No. 09/807,096 dated Jan. 15, 2010.
Official Action corresponding to U.S. Appl. No. 09/807,096 dated Apr. 3, 2006.
Official Action corresponding to U.S. Appl. No. 09/807,096 dated Jul. 7, 2005.
Official Action corresponding to U.S. Appl. No. 09/807,096 dated Jan. 27, 2005.
Official Action corresponding to U.S. Appl. No. 09/807,096 dated Sep. 23, 2004.
Somerville et al., Discovery and Characterization of a Novel, Widely Expressed Metalloprotease, ADAMTS10, and Its Proteolytic Activation. The Journal of Biological Chemistry. vol. 279, No. 49 pp. 51208-51217 (2004).
Stauber et al., "Human Tumor Necrosis Factor-( Receptor," The Journal of Biological Chemistry. vol. 263, No. 35 pp. 19098-19104 (1988).

(Continued)

*Primary Examiner* — Robert C Hayes
(74) *Attorney, Agent, or Firm* — Jenkins, Wilson, Taylor & Hunt, P.A.

(57) ABSTRACT

The invention relates to a method for producing biologically active β-NGF from the proform proNGF. After expressing the proform of the β-NGF in a prokaryotic host cell, the recombinant protein is isolated in the form of insoluble inactive aggregates (inclusion bodies). After the solubilization thereof in a strong denaturing agent and the subsequent conversion thereof into the natural conformation, which is determined by the disulfide bridges present in the natural β-NGF, biologically active β-NGF is obtained by subsequently splitting-off the prosequence.

17 Claims, 14 Drawing Sheets

(56) References Cited

OTHER PUBLICATIONS

Suenaga et al., "Renaturation of Recombinant Human Neurotrophin-3 from Inclusion Bodies Using an Aggregation Suppressor," Biotechnol. Appl. Biochem. vol. 28 pp. 119-124 (1998).

Suter et al., "Two Conserved Domains in the NGF Propeptide are Necessary and Sufficient for the Biosynthesis of Correctly Processed and Biologicall Active NGF," The EMBO Journal. vol. 10 pp. 2395-2400 (1991).

Takayama et al., Characterization of the Precursor of Prostate-specific Antigen. The Journal of Biological Chemistry. vol. 272, No. 34 pp. 21582-21588 (1987).

Yokota et al., "Biochemical and Immunocytochemical Characterization of Two Types of Myosins in Cultured Tobacco Bright Yellow-2 Cells," Plant Physiology. vol. 121 pp. 525-534 (1999).

Decision on Appeal 2012-000335 corresponding to U.S. Appl. No. 09/807,096 dated Jun. 14, 2012.

Kliemannel et al., "The mature part of proNGF induces the structure of its pro-peptide," FEBS Lett. vol. 566, pp. 207-212 (2004).

Rattenholl et al., "The pro-sequence facilitates folding of human nerve growth factor from *Escherichia coli* inclusion bodies," Eur. J. Biochem. vol. 268, pp. 3296-3303 (2001).

\* cited by examiner

SEQUENCE LISTING

<160> NUMBER OF SEQ ID NOS: 7

<210> SEQ ID NO 1
<211> LENGTH: 32
<212> TYPE: DNA
<213> ORGANISM: Artificial sequence
<220> FEATURE:
<223> OTHER INFORMATION: Artificially synthesized oligonucleotide PCR
      primer

<400> SEQUENCE: 1
cggaattcca tatggaacca cactcagaga gc                                    32

<210> SEQ ID NO 2
<211> LENGTH: 32
<212> TYPE: DNA
<213> ORGANISM: Artificial sequence

```
<220> FEATURE:
<223> OTHER INFORMATION: Artificially synthesized oligonucleotide PCR
      primer

<400> SEQUENCE: 2
ccggatcctt atcatctcac agcctttcta ga                                32

<210> SEQ ID NO 3
<211> LENGTH: 672
<212> TYPE: DNA
<213> ORGANISM: Homo sapiens
<220> FEATURE:
<221> NAME/KEY: CDS
<222> LOCATION: (1)..(666)

<400> SEQUENCE: 3 atg gaa cca cac tca gag agc aat gtc cct gca gga cac acc atc ccc       48
Met Glu Pro His Ser Glu Ser Asn Val Pro Ala Gly His Thr Ile Pro
1               5                   10                  15 caa gtc cac tgg act aaa ctt cag cat tcc ctt gac act gcc ctt cgc       96
Gln Val His Trp Thr Lys Leu Gln His Ser Leu Asp Thr Ala Leu Arg
            20                  25                  30 aga gcc cgc agc gcc ccg gca gcg gcg ata gct gca cgc gtg gcg ggg      144
Arg Ala Arg Ser Ala Pro Ala Ala Ala Ile Ala Ala Arg Val Ala Gly
        35                  40                  45 cag acc cgc aac att act gtg gac ccc agg ctg ttt aaa aag cgg cga      192
Gln Thr Arg Asn Ile Thr Val Asp Pro Arg Leu Phe Lys Lys Arg Arg
    50                  55                  60 ctc cgt tca ccc cgt gtg ctg ttt agc acc cag cct ccc cgt gaa gct      240
Leu Arg Ser Pro Arg Val Leu Phe Ser Thr Gln Pro Pro Arg Glu Ala
65                  70                  75                  80 gca gac act cag gat ctg gac ttc gag gtc ggt ggt gct gcc ccc ttc      288
Ala Asp Thr Gln Asp Leu Asp Phe Glu Val Gly Gly Ala Ala Pro Phe
                85                  90                  95 aac agg act cac agg agc aag cgc tca tca tcc cat ccc atc ttc cac      336
Asn Arg Thr His Arg Ser Lys Arg Ser Ser Ser His Pro Ile Phe His
            100                 105                 110 agg ggc gaa ttc tcg gtg tgt gac agt gtc agc gtg tgg gtt ggg gat      384
Arg Gly Glu Phe Ser Val Cys Asp Ser Val Ser Val Trp Val Gly Asp
        115                 120                 125 aag acc acc gcc aca gat atc aag ggc aag gag gtg atg gtt ttg gga      432
Lys Thr Thr Ala Thr Asp Ile Lys Gly Lys Glu Val Met Val Leu Gly
    130                 135                 140 gag gtg aac att aac aac agt gta ttc aaa cag tac ttt ttt gag acc      480
Glu Val Asn Ile Asn Asn Ser Val Phe Lys Gln Tyr Phe Phe Glu Thr
145                 150                 155                 160 aag tgc cgg gac cca aat tcc gtc gac agc ggg tgc cgg ggc att gac      528
Lys Cys Arg Asp Pro Asn Ser Val Asp Ser Gly Cys Arg Gly Ile Asp
                165                 170                 175 tca aag cac tgg aac tca tat tgt acc acg act cac acc ttt gtc aag      576
Ser Lys His Trp Asn Ser Tyr Cys Thr Thr Thr His Thr Phe Val Lys
            180                 185                 190 gcg ctg acc atg gat ggc aag cag gct gcc tgg cgg ttt atc cgg ata      624
Ala Leu Thr Met Asp Gly Lys Gln Ala Ala Trp Arg Phe Ile Arg Ile
        195                 200                 205 gat acg gcc tgt gtg tgt gtg ctc tct aga aag gct gtg aga tgataa      672
Asp Thr Ala Cys Val Cys Val Leu Ser Arg Lys Ala Val Arg
    210                 215                 220

<210> SEQ ID NO 4
<211> LENGTH: 222
<212> TYPE: PRT
<213> ORGANISM: Homo sapiens
```

-continued

<400> SEQUENCE: 4

```
Met Glu Pro His Ser Glu Ser Asn Val Pro Ala Gly His Thr Ile Pro
1               5                   10                  15

Gln Val His Trp Thr Lys Leu Gln His Ser Leu Asp Thr Ala Leu Arg
            20                  25                  30

Arg Ala Arg Ser Ala Pro Ala Ala Ala Ile Ala Arg Val Ala Gly
        35                  40                  45

Gln Thr Arg Asn Ile Thr Val Asp Pro Arg Leu Phe Lys Lys Arg Arg
    50                  55                  60

Leu Arg Ser Pro Arg Val Leu Phe Ser Thr Gln Pro Pro Arg Glu Ala
65                  70                  75                  80

Ala Asp Thr Gln Asp Leu Asp Phe Glu Val Gly Gly Ala Ala Pro Phe
                85                  90                  95

Asn Arg Thr His Arg Ser Lys Arg Ser Ser His Pro Ile Phe His
            100                 105                 110

Arg Gly Glu Phe Ser Val Cys Asp Ser Val Ser Val Trp Val Gly Asp
        115                 120                 125

Lys Thr Thr Ala Thr Asp Ile Lys Gly Lys Glu Val Met Val Leu Gly
    130                 135                 140

Glu Val Asn Ile Asn Asn Ser Val Phe Lys Gln Tyr Phe Phe Glu Thr
145                 150                 155                 160

Lys Cys Arg Asp Pro Asn Ser Val Asp Ser Gly Cys Arg Gly Ile Asp
                165                 170                 175

Ser Lys His Trp Asn Ser Tyr Cys Thr Thr Thr His Thr Phe Val Lys
            180                 185                 190

Ala Leu Thr Met Asp Gly Lys Gln Ala Ala Trp Arg Phe Ile Arg Ile
        195                 200                 205

Asp Thr Ala Cys Val Cys Val Leu Ser Arg Lys Ala Val Arg
    210                 215                 220
```

<210> SEQ ID NO 5
<211> LENGTH: 7
<212> TYPE: PRT
<213> ORGANISM: Homo sapiens

<400> SEQUENCE: 5

```
Met Glu Pro His Ser Glu Ser
1               5
```

<210> SEQ ID NO 6
<211> LENGTH: 6
<212> TYPE: PRT
<213> ORGANISM: Homo sapiens

<400> SEQUENCE: 6

```
Arg Val Ala Lys Arg Ser
1               5
```

<210> SEQ ID NO 7
<211> LENGTH: 9
<212> TYPE: PRT
<213> ORGANISM: Homo sapiens

<400> SEQUENCE: 7

```
Met Glu Pro His Ser Glu Ser Asn Val
1               5
```

METHOD FOR OBTAINING ACTIVE PRO-NGF AND BETA-NGF

CROSS REFERENCE TO RELATED APPLICATIONS

This application is a divisional of U.S. patent application Ser. No. 09/807,096, filed Nov. 19, 2001, now U.S. Pat. No. 8,318,671, which itself is a national stage application of PCT International Patent Application Serial No. PCT/EP99/07613, filed Oct. 11, 1999, which itself claimed priority to European Patent Application Serial No. 98119077.0, filed Oct. 9, 1998. The disclosure of each of these applications is incorporated by reference in its entirety.

The present invention relates to a method for the preparation of β-NGF by naturation of denatured inactive proNGF and cleavage of the pro sequence.

Nerve growth factor (β-NGF) is a neurotrophic factor required for the growth and survival of sympathetic and sensory neurons (Levi-Montalcini, R., Science 237 (1987) 1154; Thoenen, H., et al., Physiol. Rev. 60 (1980) 1284; Yankner, B. A., et al., Annu. Rev. Biochem. 51 (1982) 845). Furthermore, β-NGF promotes the growth, differentiation and vitality of cholinergic neurons of the central nervous system (Hefti, F. J., J. Neurobiol. 25 (1994) 1418). Possible therapeutic indications for recombinant human nerve growth factor include peripheral sensory neuropathies, e.g. associated with diabetes or as a possible side effect in AIDS therapy. Other indications for rh β-NGF are central neuropathies, e.g. Alzheimer's disease. In this case, the loss of memory is the result of a loss of cholinergic neurons.

Human β-NGF is translated as a preprotein consisting of 241 amino acids. The prepeptide (18 amino acids) is cleaved off during translocation into the endoplasmic reticulum (ER), while the resulting proprotein is subsequently processed at its N an C terminus (removal of the prosequence (103 amino acids) and the last two amino acids). Therefore, mature human NGF contains 118 amino acids. It shows homology to murine β-NGF and differs from this protein only by 12 amino acid exchanges. For conducting clinical studies or a possible use as therapeutic, the β-NGFs must be available in high amounts. A natural source of higher amounts of this factor are the submaxillary glands of mice. These preparations, however, are heterogeneous mixtures of different dimers and are unsuitable for therapeutic use. Furthermore, it is desirable to administer the human form of the protein to the patients. In human tissue, however, neurotrophic factors are present only in minute concentrations.

Therefore, to use β-NGF as a therapeutic agent the preparation of the protein by means of recombination is the only possibility. This may be achieved in two ways: by a recombinant expression either in cell cultures or in bacteria. Eukaryotic cell expression systems tend to provide only very low amount of proteins and are relatively expensive (Barnett, J., et al., J. Neurochem. 57 (1991) 1052; Schmelzer, C. H., et al., J. Neurochem. 59 (1992) 1675; U.S. Pat. No. 5,683,894).

In contrast, prokaryotic expression systems provide high amounts of the desired protein. However, in contrast to eukaryotic expression systems bacteria are unable to process the precursor proteins in the correct manner. As in the expression of many other recombinant mammalian genes, the production of recombinant β-NGFs in bacteria results in a biologically inactive translation product which is then accumulated in the cell in the form of aggregates (so-called inclusion bodies (IBs)).

Naturation of mature β-NGF from such inclusion bodies, however, is only possible in the case of very low protein concentrations (below 10 µg/ml) and very low yields (up to about 10%). Such methods are for example described in EP-A 0 544 293, U.S. Pat. No. 5,606,031, U.S. Pat. No. 5,235,043, as well as WO 97/47735. The naturation via sulfitolysis of neurotrophic factors of the NGF/BDNF family is described in WO 95/30686.

In WO 97/47735 there is described an improved method for the naturation of proteins. In this method, the inactive protein is dissolved in a solution of a denaturing agent having a denaturing concentration in the presence of a low molecular weight substance which contains thiol groups. Afterwards, the dissolved protein is transferred from the strongly denaturing solution into another solution which is not or only weakly denaturing in which it assumes a biologically active conformation wherein the disulfide bonds are opened by means of the thiol component and subsequently are formed newly in the protein in a manner that the protein assumes a conformation which has biological activity. Using an improved method of this type, a yield of naturation of β-NGF of about 10% may be achieved.

It is an object of the present invention to provide an improved method for the preparation of β-NGF which is simple and provides active NGF in a high yield.

This object has been solved by providing a method for the preparation of a biologically active β-NGF by means of naturation of the pro form present in its inactive form and having a very poor solubility wherein the pro form preferably is available in the form of inclusion bodies after recombinant preparation in prokaryotes, said method being characterized by dissolving proNGF in its inactive form which has a poor solubility in a solution of a denaturing agent in a denaturing concentration, transferring proNGF into a solution which is not or weakly denaturing maintaining the solubility wherein the dissolved denatured proNGF assumes a biologically active conformation which is determined by the disulfide bonds present in the native NGF, and afterwards removing the prosequence whereby active NGF is obtained which may be isolated.

Surprisingly, it has been shown that during naturation of inactive β-NGF in vitro the prosequence has an essential and positive effect on the naturation process and according to the present invention it is possible to perform the renaturation in the most simple manner and thereby achieve yields of natured active β-NGF which have not been known so far and have not been deemed possible.

The term "proNGF" means β-NGF which is linked to its prosequence at its N terminus. According to the present invention, there may be used as said prosequence either the whole prosequence (U.S. Pat. No. 5,683,894; Ullrich, A., et al., Nature 303 (1983) 821; SWISS-PROT protein sequence database No. P01138) or portions thereof, preferably complete domains. Suter et al. (EMBO J. 10, 2395 (1991)) have performed a detailed study of the in vivo function of the propeptide of murine β-NGF on the basis of correct secretion in a COS-7 cell culture system. For this purpose, the prosequence has been divided into five regions. Mutants have been prepared having deletions in one or more of these sequences. It has been found that the sequence regions containing amino acids −52 to −26 ("domain I") as well as −6 to −1 ("domain 11") are essential for the expression and secretion of biologically active β-NGF. Domain I is essential for the expression while domain II is required for correct proteolytic processing. Surprisingly, it has been shown that proNGF has an activity in vivo analogous to β-NGF. Therefore, proNGF may also be used as a therapeutic.

Inactive proNGF showing a poor solubility is formed during overexpression of the protein in the cytosol of prokaryotes. In this case, proNGF prepared by recombination remains in the cytoplasm in an insoluble and aggregated form. These protein aggregates, the isolation thereof as well as their purification are described for example in Marston, F. A., Biochem. J. 240 (1986). To isolate these inactive protein aggregates (inclusion bodies) the prokaryotic cells are disrupted following fermentation.

Cell disruption may be performed by conventional methods, e.g. by means of sonication, high pressure dispersion or lysozyme (Rudolph, R., et ale (1997); Folding proteins. In: Creighton, T. E. (ed.): Protein Function: A Practical—Approach. Oxford University Press, pp. 57-99). It is preferably carried out in a buffer solution suitable to adjust a neutral to weakly acidic pH value and serving as a suspension medium, such as 0.1 mol/l Tris/HCl. After cell disruption, the insoluble components (inclusion bodies) are removed in any suitable manner, preferably by centrifugation or filtration following one or more washing steps with agents that leave IBs intact but possibly dissolve foreign cellular proteins, e.g. in water or phosphate buffer, optionally with mild detergents added such as Brij®. Afterwards the insoluble fraction (pellet) is subjected to the method according to the present invention for solubilization and naturation.

As the denaturing agent there is conveniently used a denaturing agent usually employed in the solubilization of inclusion body proteins. Guanidinium hydrochloride and other guanidinium salts, such as the thiocyanate as well as urea and its derivatives are preferably used. Moreover, mixtures of these denaturing agents may be used.

The concentration of the denaturing agent is dependent on the type of denaturing agent and can be determined easily by the skilled artisan. The concentration of the denaturing agent (denaturing concentration) is sufficient if complete solubilization of the denatured protein having a poor solubility may be achieved. For guanidinium hydrochloride, these concentrations usually are in the range of 3 to 8 mol/l, preferably 5 to 7 mol/l. For urea, the concentrations usually are in the range of 6 to 10 mol/l. A weekly denaturing solution is a solution which contains a denaturing agent in a concentration enabling formation of the correct disulfide bonds in the protein and thereby the formation of the native tertiary structure of the protein. Preferably, strongly and weakly denaturing solutions differ in their concentrations by a factor of 100 or more.

Furthermore, for complete monomerization of the inclusion body proteins it is advantageous to also add during the solubilization a reduction agent such as dithiothreitol (DTT), dithioerythritol (DTE) or 2-mercaptoethanol in a concentration of 10-400 mM and particularly preferred in a concentration of 20-100 mM.

Following solubilization a dialysis is performed, preferably against a solution which contains a denaturing agent in a denaturing concentration in order to remove the reduction agent which may optionally be present. Conveniently, the solution against which dialysis is carried out contains the denaturing agent in the same concentration as present in the denaturing solution.

Subsequent naturation according to the method of the present invention is performed at a pH in the neutral to alkaline range, preferably between pH 7 and 10, particularly preferred in a pH range between 7.5 and 9.5. As the buffer solutions, any conventional buffer may be used. Preferably, buffers known to those skilled in the art such as Tris or phosphate buffers are used as the renaturing agents. To transfer the denatured protein into renaturation buffer, the solubilized protein is either diluted into the renaturation buffer or dialyzed against renaturation buffer. Thereby, the concentration of the denaturing agent is also diluted (weakly denaturing solution) so that no further denaturation of the protein occurs. Already during initial reduction of the concentration of the denaturing agent a renaturing process may occur. The conditions for transfer of the protein into the solution which is not or only weakly denaturing must be properly selected to ensure that the protein substantially remains in solution. Conveniently, this may be achieved by a slow continuous or a stepwise dilution. It is preferred to dilute the denaturing agent in a manner that the naturation of the protein is as complete as possible or the denaturing agent is almost completely removed, e.g. by dialysis.

Preferably, naturation is performed in the presence of low molecular weight auxiliary agents having a positive effect on the yield upon naturation. Such auxiliary agents are for example described in U.S. Pat. No. 5,593,865. Particularly preferred as the low molecular weight auxiliary agent during naturation is arginine, conveniently in a concentration of 0.2 to 1.5 M.

According to the method of the present invention, naturation is preferably performed by adding a thiol component in its reduced and oxidized forms. Preferred thiol components include glutathion in the reduced (GSH) and oxidized form (GSSG), cysteamine and cystamine, cysteine and cystine or 2-mercaptoethanol and 2-hydroxy ethyldisulfide. By addition of these thiol reagents in reduced and oxidized forms it is possible to achieve the formation of disulfide bonds within the folding polypeptide chain during renaturation as well as "reshuffling" of wrong disulfide bonds within or between the folding polypeptide chains (Rudolph et al., 1997, loc. cit.).

Conveniently, the method according to the present invention is performed during naturation at low temperatures (preferably at about 10° C.). In the course of the method according to the present invention the renaturation is performed for a period of 0.5 to 5 h, preferably 1 to 2 h.

To prevent oxidation of the reducing agent by oxygen present in the air and to protect free SH groups it is convenient to add a complexing agent such as EDTA, preferably in an amount of 1-20 mM, particularly preferred at about 10 mM.

The term "activity of $\beta$-NGF" means the biological activity of $\beta$-NGF. Biologically active $\beta$-NGF exists in the form of a dimer. The activity may be determined according to the DRG assay (dorsal root ganglion assay), Levi-Montalcini, R., et al., Cancer Res. 14 (1954) 49, and Varon, S., et al., Meth. in Neurochemistry 3 (9172) 203. In this assay the stimulation and survival of sensory neurons from dissociated dorsal root ganglia of chick embryos is monitored by means of neurite formation.

The prosequence is a domain separate from the mature protein. Between these two domains there is an exposed protease cleavage site. These cleavage sites may be specifically processed by suitable proteases. For example, trypsin cleaves after basic amino acids such as lysine or arginine. If the ratio of proNGF to trypsin is appropriately adjusted, the correctly folded, mature protein will not be cleaved by this protease. In contrast, denatured proteins as well as folding intermediates expose sequences which are susceptible to an attack by the protease. Proteases having a trypsin-like substrate specificity are preferred for processing of proNGF. These proteases cleave the protein without digesting the active portion of the protein molecule. As the trypsin-like proteases, several serine proteases (e.g. trypsin itself or $\gamma$-NGF) are considered. Trypsin is preferably used. For limited proteolysis, the protein is employed in a mass ratio of 1:40 to 1:2500 (trypsin:proNGF ratio), preferably in a range of 1:40 to 1:250. The proteolysis is carried out using an incubation time of 1 min to 24 h, preferably 1 to 60 min at a temperature of 0° C. to 37° C., preferably 0° C. to 20° C. As the buffers there are used buffers which do not inhibit the activity of the protease. Phosphate and Tris buffer in a concentration range of 10-100 mM are preferred. The limited proteolysis is performed in the optimal pH range of the protease; a medium of pH 7-8 is preferred. After completion of the incubation time the proteolysis is stopped either by addition of a specific inhibitor, preferably 1 to 5 mM PMSF (phenylmethylsulfonylfluoride) or soy bean trypsin inhibitor, preferably 1 mg per 0.1 to 5 mg trypsin, or by reduction of the pH to 2-3 by addition of an acid, preferably HCl (Rudolph, R., et al. (1997); Folding proteins. In: Creighton, T. E. (ed.): Protein Function: A Practical Approach. Oxford University Press, pp. 57-99; U.S. Pat. No. 5,683,894).

The following Examples, publications and Figures further illustrate the present invention the scope of which is obvious from the present Claims. The processes described are meant to be exemplary and describe the object of the present invention also following modification.

Figure 2:
FIG. 2 shows a Coomassie stain of an SDS PAGE gel (15%) of crude extracts of E. coli strain BL21 (DE3) pET11a-proNGF/pUBS520 prior to and after induction, respectively, as well as of an IB preparation (SDS PAGE according to Laemmli, UK, Nature 227 (1970) 680). U: crude extract prior to induction, I: crude extract after four hours induction, P: IB pellet, S: soluble supernatant).
Figure 2A:
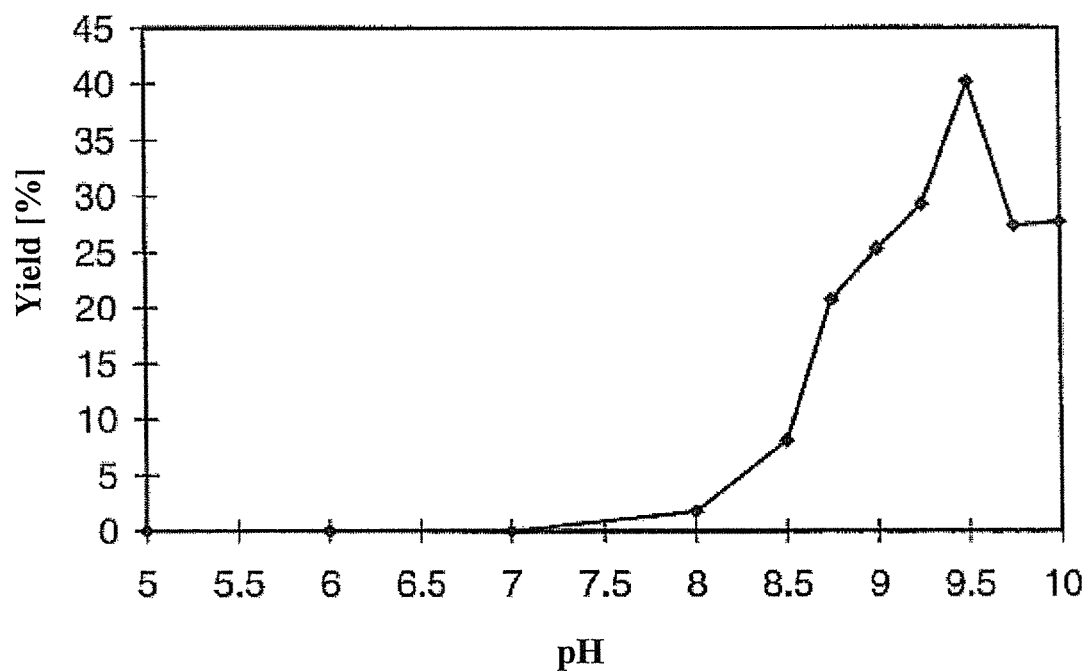

FIG. 2a shows the effect of the pH value on the folding of rh proNGF at 10° C. in 100 mM Tris/HCl, 1 M L-arginine, 5 mM GSH, 1 mM GSSG, 5 mM EDTA. The protein concentration was 50 µg/ml, the folding period was 3 hours. The mean values of two measuring series are shown.

Figure 2B:
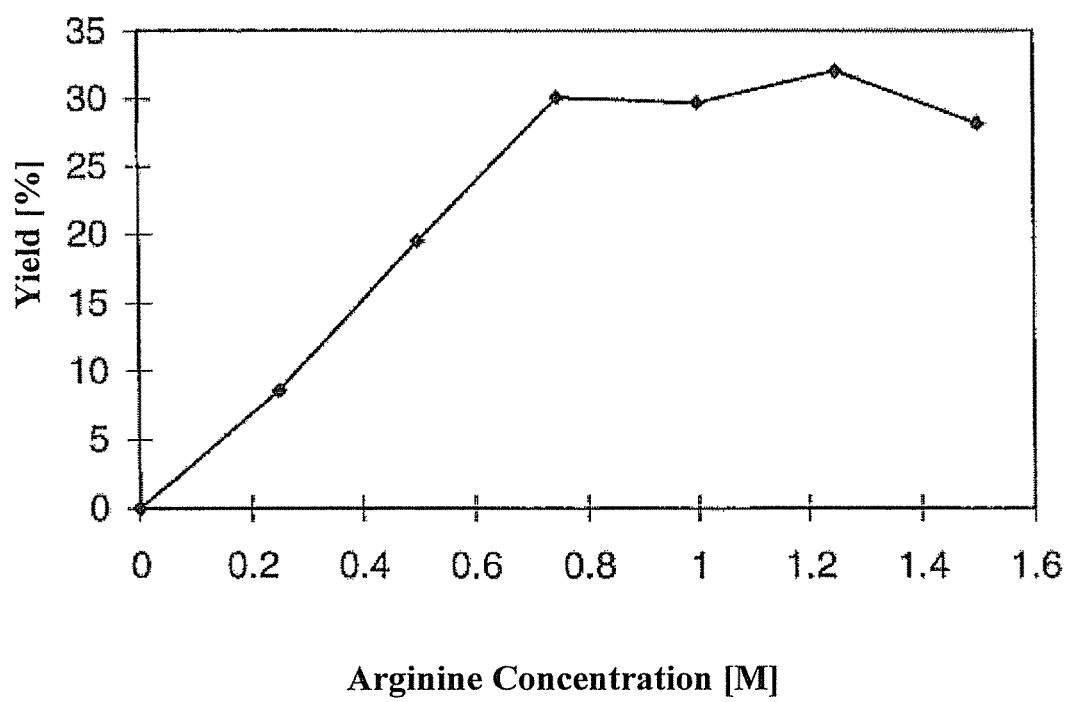

FIG. 2b represents the effect of different concentrations of L-arginine on the folding of rh proNGF. Renaturation took place at a pH of 9.5, the other conditions were identical to those used in pH variation. The mean values of two measuring series are shown.

Figure 2C:
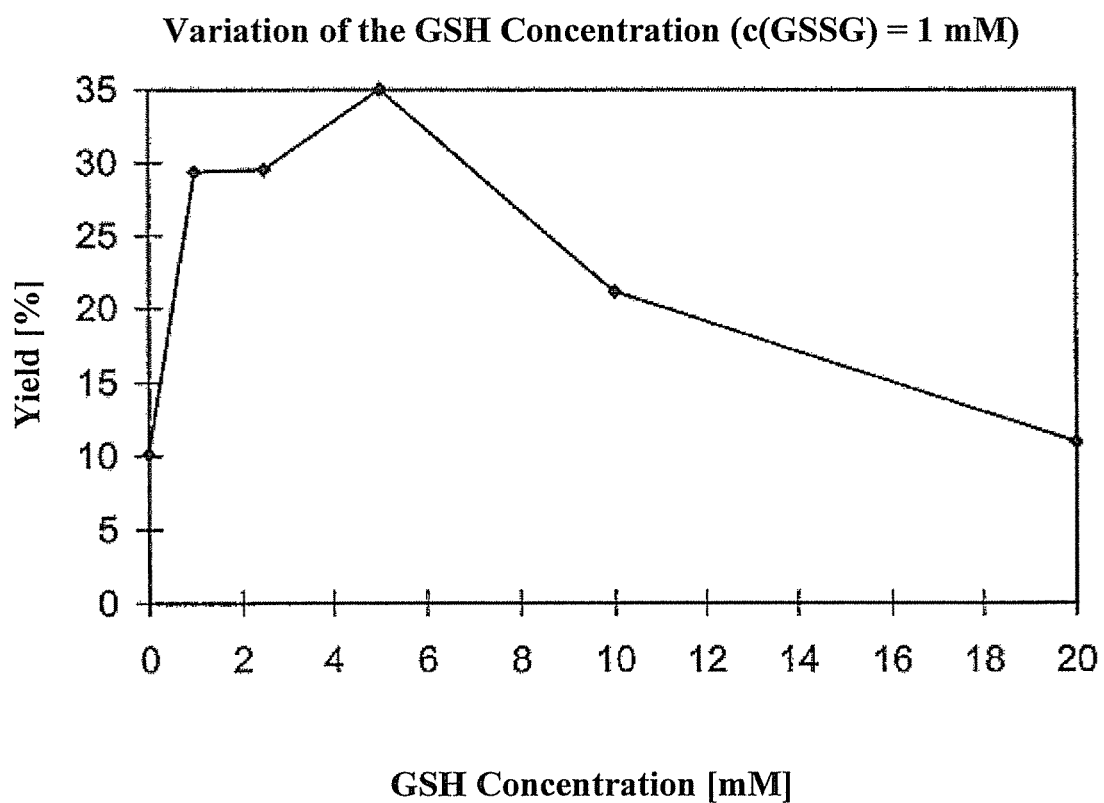

FIG. 2c shows the effect of different GSH concentrations on the folding of rh proNGF. The concentration of GSSG was 1 mM, the L-arginine concentration 1 M. The other parameters of renaturation were identical to those used in arginine variation. The mean values of two measuring series are shown.

Figure 2D:
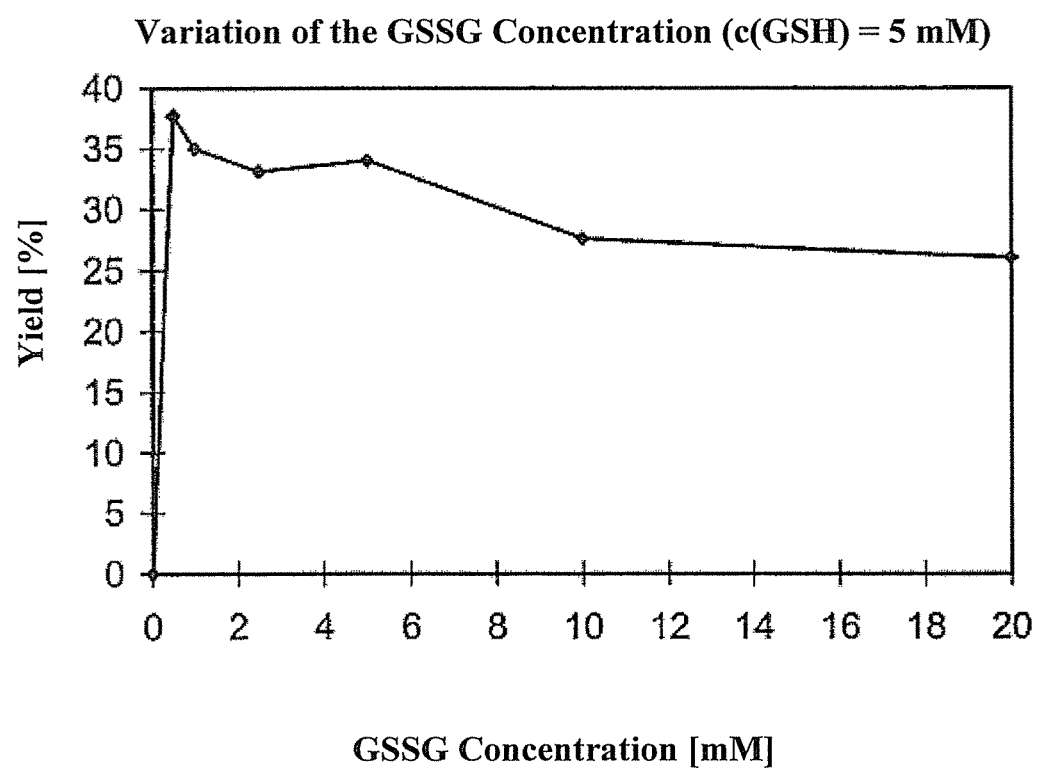

FIG. 2d shows the effect of different GSSG concentrations on the folding of rh proNGF. The concentration of GSH was 5 mM. The other folding parameters were identical to those used in GSH variation. The mean values of two measuring series are shown.

Figure 2E:
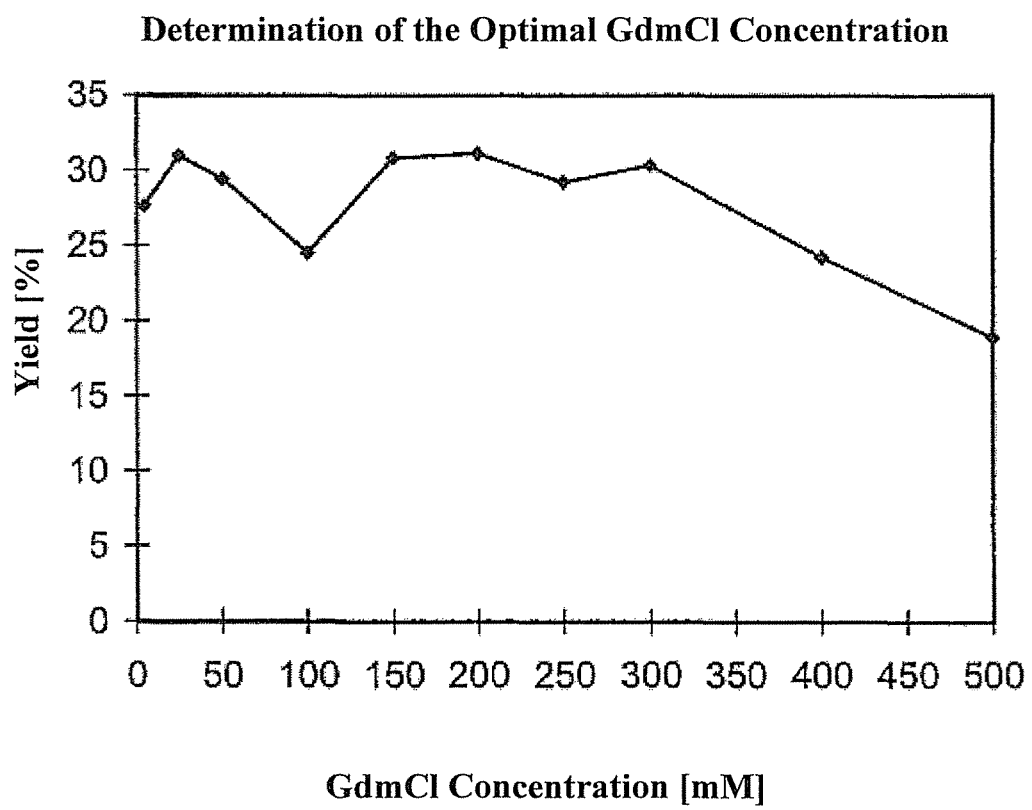

FIG. 2e shows the effect of different amounts of GdmCl on the yield of native rh proNGF. The amount of GSH and GSSG was 5 mM and 0.5 mM, respectively. The other renaturation conditions were identical to those used in GSSG variation. The mean values of two measuring series are shown.

Figure 2F:
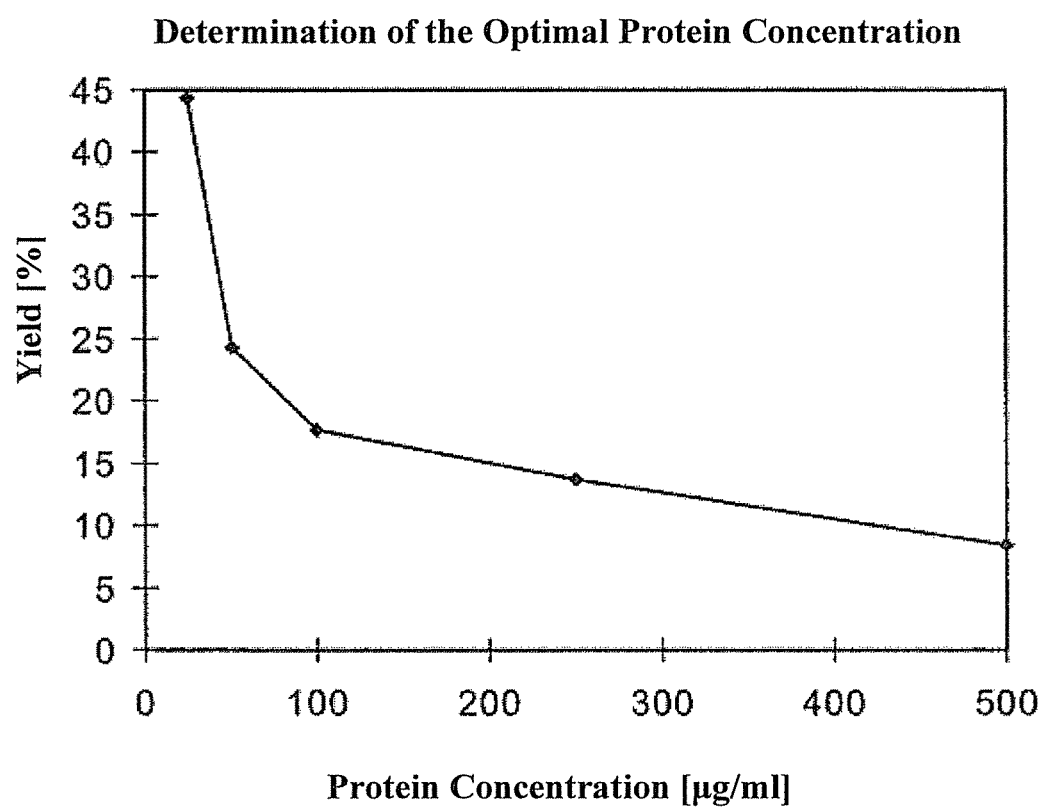

FIG. 2f shows the effect of different protein concentrations on the yield of folding of rh proNGF. In all samples, the concentration of GdmCl was 200 mM. All other folding parameters were identical to those used in GdmCl variation. A single measuring series is shown.

Figure 3:
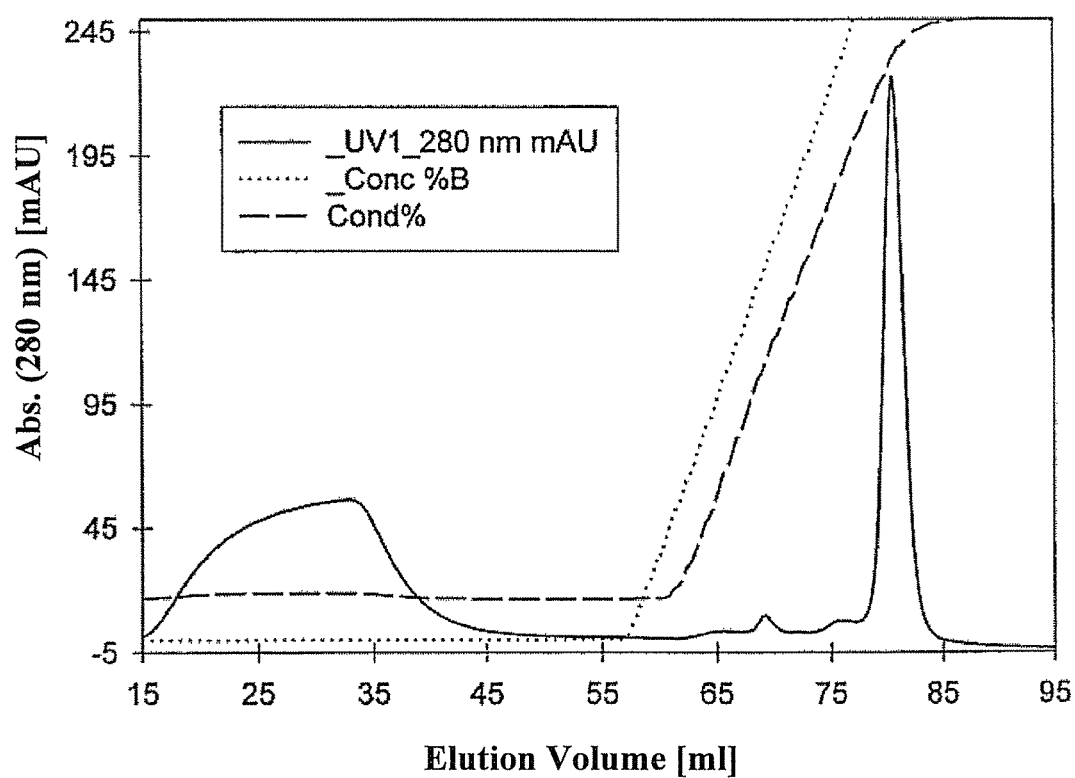

FIG. 3 shows the elution profile of the purification of rh proNGF by means of cation exchange chromatography on Poros 20 HS (Perseptive Biosystems, column volume 1.7 ml).

Figure 4:
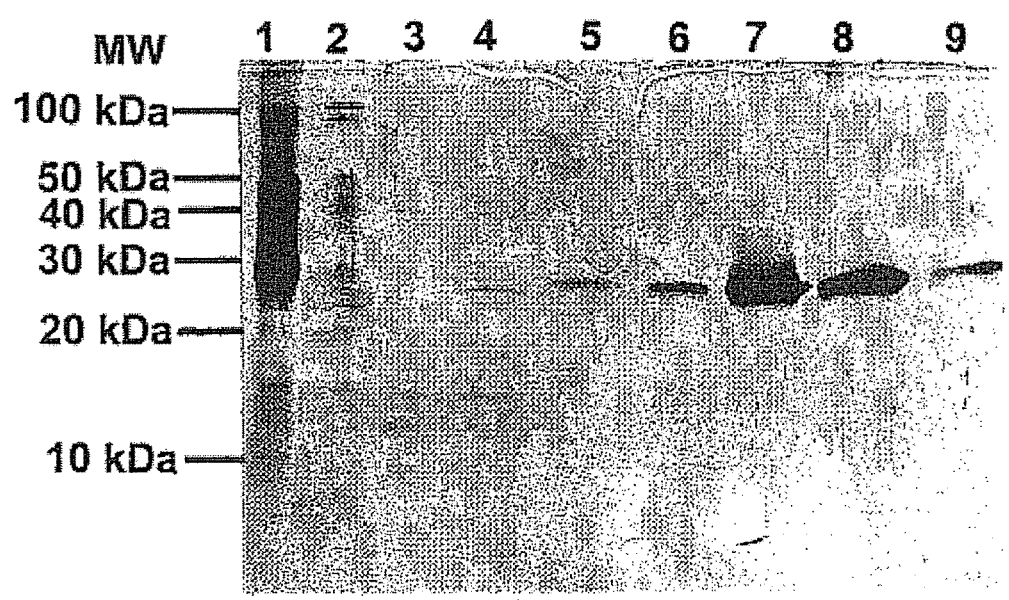

FIG. 4 shows an SDS PAGE gel (15%, silver stain according to Nesterenko, M. V., et al., J. Biochem. Biophys. Methods 28 (1994) 239) of the purification of rh proNGF on Poros 20 HS (1: renatured proNGF as loaded to the column; 2: void; 3: fraction 4 (66 to 69 ml); 4: fraction 5 (69 to 72 ml); 5: fraction 6 (72 to 75 ml); 6: fraction 7 (75 to 78 ml); 7: fraction 8 (78 to 81 ml); 8: fraction 9 (81 to 84 ml); 9: fraction 10 (84 to 87 ml)).

Figure 5:
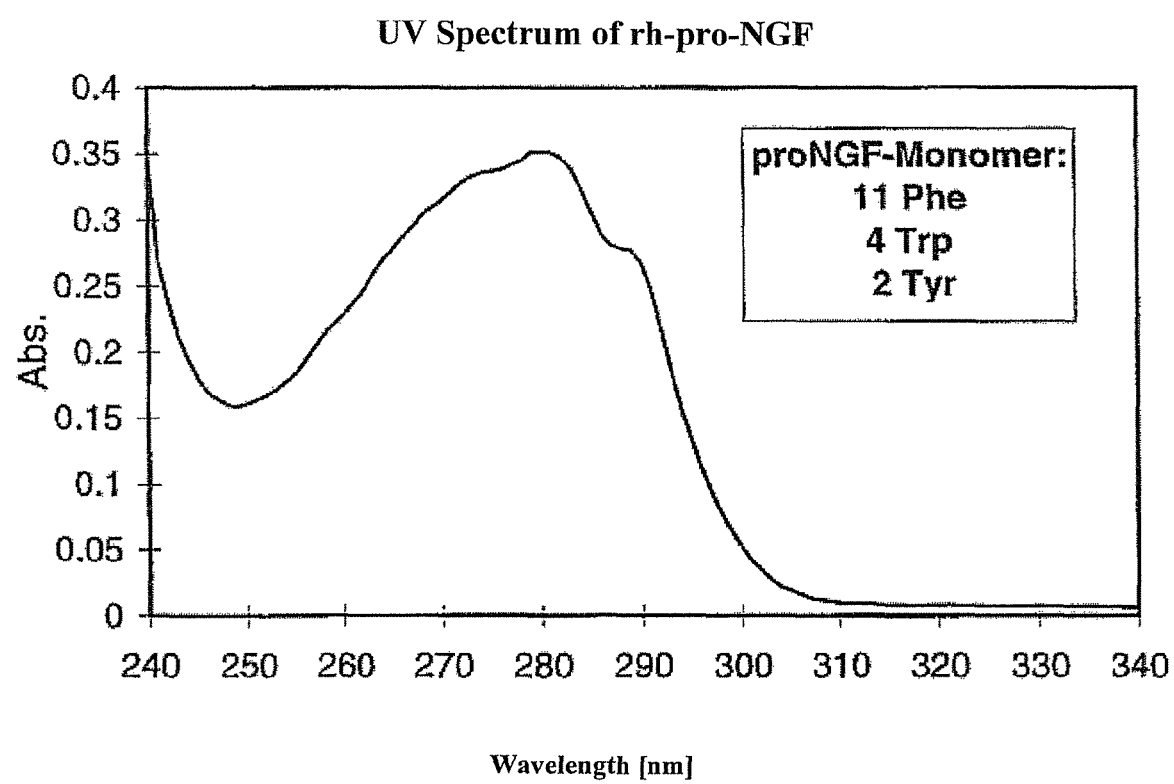

FIG. 5 shows the UV spectrum of rh proNGF.

Figure 6:
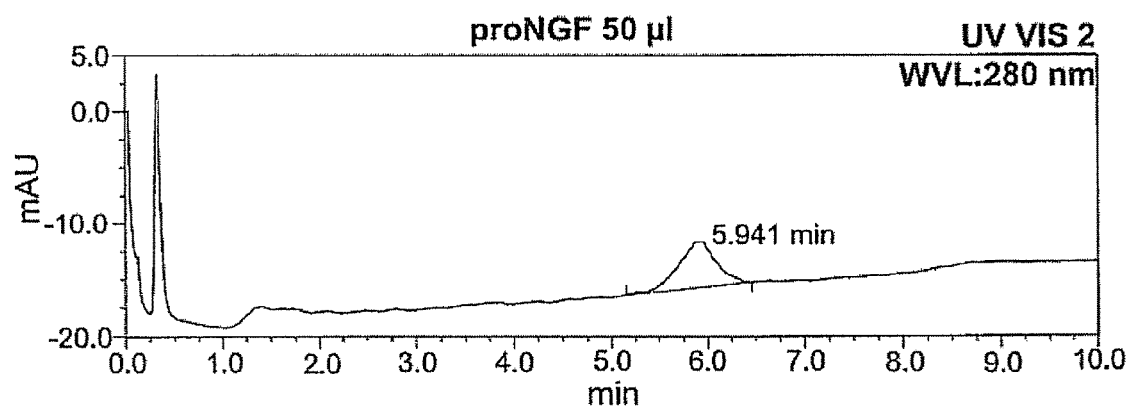

FIG. 6 shows an IEX-HPLC elution diagram of rh proNGF (column material: Poros 20 HS, 100 mm×4.6 mm column, Perseptive Biosystems company).

Figure 7:
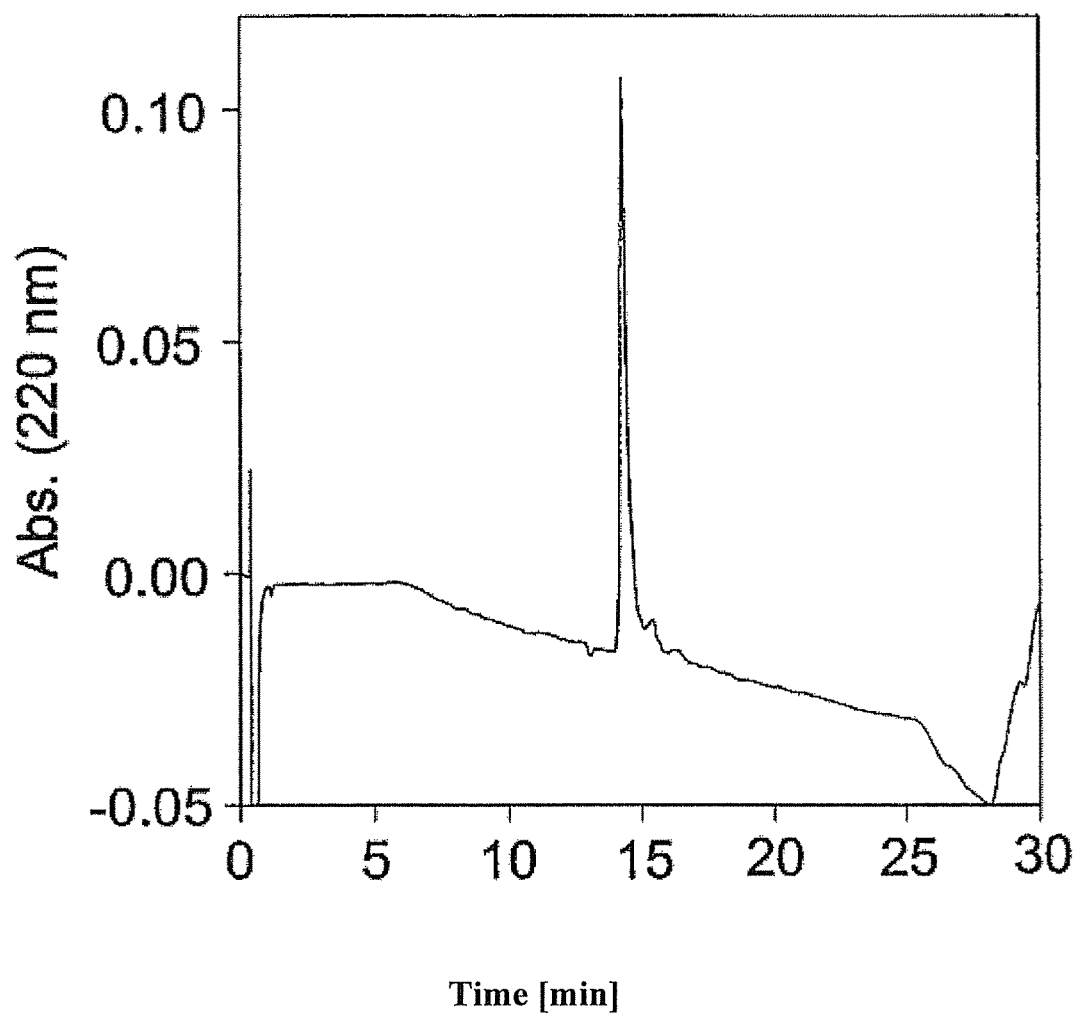

FIG. 7 shown an RP-HPLC elution diagram of rh proNGF (column material: Poros 10 R1, 100 mm×4.6 mm column, Perseptive Biosystems company).

Figure 8:
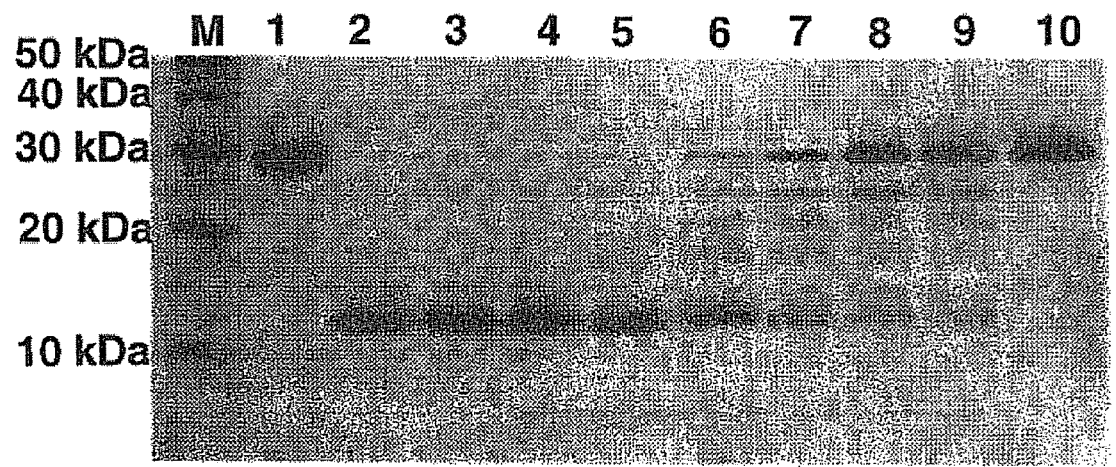

FIG. 8 shows an SDS gel (15% Coomassie stain) of the limited proteolysis of rh proNGF with trypsin (M: 10 kDA marker, 1: rh proNGF standard; 2: rh β-NGF standard; 3: mass ratio trypsin:rh proNGF≈1:40, 4:1:100, 5:1:250, 6:1:500, 7:1:1000, 8:1:2000, 9:1:2500, 10: control without trypsin, with STI).

SEQ ID NO: 1 and 2 show oligonucleotides for the construction of pET11a-proNGF.

SEQ ID NO: 3 shows the nucleotide sequence of the cDNA of human proNGF as well as the amino acid sequence of the translation product.

SEQ ID NO: 4 shows the amino acid sequence of the translation product.

EXAMPLE 1

Cloning of the cDNA Encoding proNGF into an E. Coli Expression Vector

For the cloning of the proNGF construct the T7 expression system of Novagen was chosen (Studier, F. U., et al., J. Mol. Biol. 189 (1986) 113). The DNA sequence encoding proNGF is under the control of the strong T7 transcription signal. As the host strain, E. coli BL21 (DE3) is used. The chromosome contains the gene for T7 RNA polymerase. Expression of this RNA polymerase and thereby of the proNGF is induced by IPTG (isopropyl-β-D-thiogalactoside).

Figure 1:
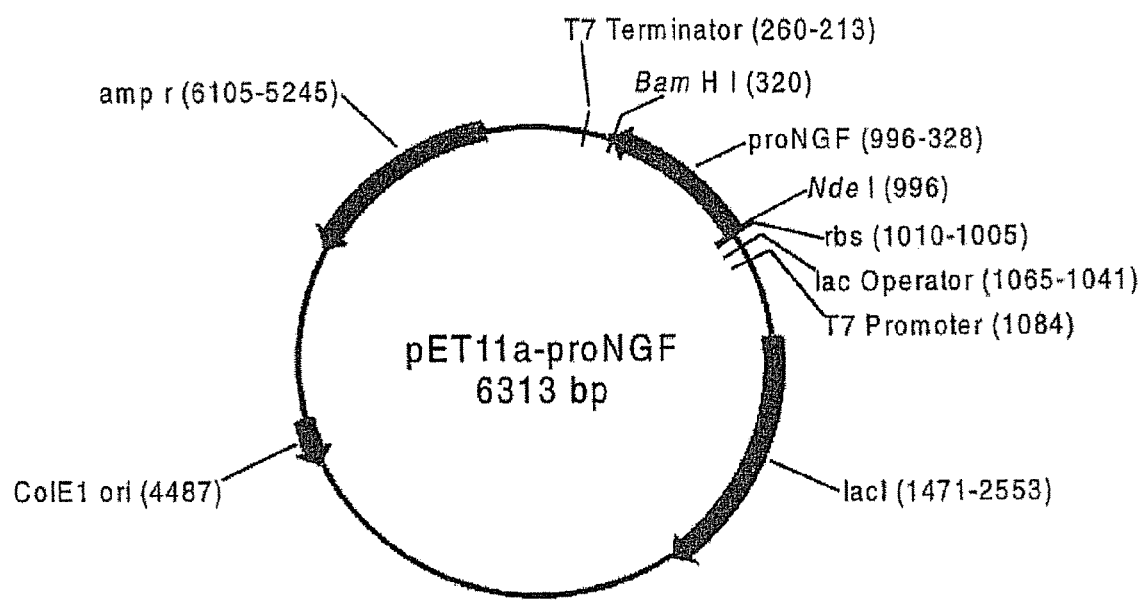
FIG. 1 shows the proNGF plasmid construct pET11a-proNGF for the expression of recombinant human proNGF.

The cDNA for human proNGF was obtained by PCR amplification from vector pMGL-SIG-proNGF of Boehringer Mannheim (PL No. 1905). At the 5' end of the DNA sequence encoding proNGF an NdeI restriction site and at the 3' end a BamHI restriction site were introduced using mutagenesis primers. The peR product was inserted into the NdeI/BamHI restriction site of the multiple cloning region of vector pET1la (Novagen) (FIG. 1).

The following primers were used in the PCR:

```
Forward primer "FwProNGF":
                                         (SEQ ID NO: 1)
5'-CG GAA TTC CA|T ATG GAA CCA CAC TCA GAG AGC-3'
                                         (SEQ ID NO: 5)
               Met Glu Pro His Ser Glu Ser Reverse primer "RevNGF":
                                         (SEQ ID NO: 2)
5'-CC G|GA TCC TTA TCA TCT CAC AGC CTT TCT AGA-3'
                                         (SEQ ID NO: 6)
           stop stop Arg Val Ala Lys Arg Ser
```

After cloning into the vector, the nucleotide sequence was verified by means of DNA sequencing.

EXAMPLE 2 a) Expression of Human proNGF in E. Coli

For culturing of the recombinant bacterial strain an overnight culture was prepared. For this purpose a suitable volume of LB medium was added with 100 µg/ml ampicillin and 50 µg/ml kanamycin.

LB medium (1 l): 10 g trypton
    10 g yeast extract
    5 g NaCl

The medium was inoculated with a single colony and agitated over night at 37° C.

The next morning, the desired volume of 2×YT medium containing 100 µg/ml ampicillin and 50 µg/ml kanamycin was inoculated with the overnight culture in a ratio of 1:100 (v/v). The culture was agitated at 37° C. and 200-250 rpm until $OD_{600}$ of 0.5-0.8 was reached. Afterwards, the expression of proNGF was induced by 3 mM IPTG for 4 h at the same temperature. Subsequently, the cells were harvested by centrifugation and either disrupted immediately or stored frozen at −70° C.

2ΔYT medium (1 l): 17 g trypton
    10 g yeast extract
    5 g NaCl b) Isolation of IBs In the bacterial cells the recombinant protein is present in the form of aggregates. The preparation of these "inclusion bodies" was performed according to Rudolph, R., et al. (1987); Folding proteins. In: Creighton, T. E. (ed.): Protein Function: A Practical Approach. Oxford University Press, pp. 57-99.

For cell disruption, 5 g each of the cell pellet were resuspended in 25 ml of 100 mM Tris/HCl pH 7.0; 1 mM EDTA. Afterwards, 1.5 mg of lysozyme were added per g of wet cell mass, incubated for 30 min at 4° C., and subsequently the cells were disrupted using a Gaulin cell disruptor. Then, 3 mM of $MgCl_2$ as well as 10 µg/ml DNase were added to the crude homogenate and incubated for 30 min at 25° C. After DNase digestion the insoluble cell components were solubilized by addition of 0.5 volumes 60 mM EDTA, 6% Triton X-100, 1.5 M NaCl pH 7.0 followed by incubation for 30 minutes at 4° C. The IBs were collected by centrifugation for 10 min at 13,000 rpm. Afterwards, they were washed four times each with 100 ml of 100 mM Tris/HCl pH 7.0; 20 mM EDTA and stored at −20° C.

In this manner, about 4 g of IB pellet could be reproducibly obtained from 10 l of E. coli culture (about 44 g wet cell weight). The preparations always contained approx. 90-95% rh proNGF (FIG. 2).

EXAMPLE 3 a) Solubilization of IBs 400 mg of IB pellet were suspended in 2 ml solubilization buffer (100 mM Tris/HCl pH 8.0; 6 mM GdmCl; 100 mM DTT; 10 mM EDTA), incubated for 2 h at 25° C. and centrifuged for 30 min at 13,000 rpm in the cold room. Afterwards, the supernatant was removed and adjusted to pH 3-4 with 1 M HCl. The solubilized material was dialyzed three times each against 300 ml 6 M GdmCl pH 4.0, 10 mM EDTA, i.e. twice for 2 h each at 25° C. and once over night in the cold room (12° C., 16-18 h). The protein concentration was then determined using the method of Bradford (Bradford, M. M., Anal. Biochem. 72 (1976) 248). The concentration of rh proNGF was between 40 and 50 mg/ml.

b) Optimizing the Renaturation of rh proNGF

To prepare biologically active rh proNGF from the solubilized materials prepared in Example 3a) these were diluted into different renaturation buffers. To determine the optimal folding conditions, the following parameters were varied in the order listed:

a) temperature and time
b) pH
c) arginine concentration
d) GSH/GSSG concentration
e) GdmCl concentration
f) protein concentration The results are presented in Tables 1 and 2 as well as in FIGS. 2a-f. The amount of renatured proNGF in the folding samples was determined by RP-HPLC. For this purpose, 925 µl each of the folding samples were removed at predetermined time points and treated with 75 µl of 32% HCl to stop the folding reaction. For RP-HPLC analytics a Poros 10 R1 HPLC column and the Beckman Gold HPLC system with solvent module 125 NM, detector 168, autosampler 507, and analysis software "Gold V 8.10" were used. The elution peaks obtained were fitted using the "peakfit" program version 2.01. For a quantitative determination of the yields, a standard graph was constructed using purified native rh proNGF. Since the rh proNGF IBs were very pure, the total amount of protein employed in the renaturation samples was equated with the amount of rh proNGF for the quantitative analysis. The measurement results shown are mean values of two measurements each.

TABLE 1

| Temperature [° C.] | Overall yield [%] | No further increase after about | rate constant k $[s^{-1}]$ |
|---|---|---|---|
| 4 | 25.8 | 3.3 h | $2.569 \times 10^{-4} s^{-1}$ |
| 10 | 29.0 | 1.6 h | $4.865 \times 10^{-4} s^{-1}$ |
| 15 | 22.4 | 1.1 h | $6.399 \times 10^{-4} s^{-1}$ |
| 20 | 12.0 | 1.0 h | $1.065 \times 10^{-4} s^{-1}$ |
| 25 | 11.4 | 0.8 h | $1.935 \times 10^{-4} s^{-1}$ |

Determination of the optimal temperature and time during rh proNGF folding. The protein concentration in each of the renaturation samples was 50 µg/ml. The folding buffer consisted of
100 mM Tris/HCl pH 9.5
1 M L-arginine
5 mM GSH
1 mM GSSG
5 mM EDTA
The measurement series were performed several times and fitted using an exponential function. The mean values of two measurements are shown.

TABLE 2

| No. of sample | ratio GSH/GSSG [mM] | yield [%] |
|---|---|---|
| 1 | 5/0.5 | 37.7 |
| 2 | 5/1 | 35.0 |
| 3 | 5/5 | 34.0 |
| 4 | 5/2.5 | 33.1 |
| 5 | 1/1 | 29.4 |
| 6 | 5/10 | 27.6 |
| 7 | 5/20 | 26.0 |
| 8 | 205/1 | 22.1 |
| 9 | 10/1 | 21.2 |
| 10 | 1/5 | 18.9 |
| 11 | 20/1 | 10.9 |
| 12 | 0/1 | 9.85 |
| 13 | 0/0 | 0 |
| 14 | 5/0 | 0 |

This Table shows the effect of different concentrations of GSH/GSSG (GSH = reduced glutathione GSSG = oxidized glutathione) on the folding of rh proNGF. The renaturation buffer used was
100 mM Tris/HCl pH 9.5
1 M L-arginine
5 mM EDTA
The folding time was 3 h at 10° C. In the Table, the individual folding samples are presented in the order of decreasing yield. The mean yields of two measurement series are shown.

c) Renaturation of rh proNGf in the Preparative Scale

Rh proNGF was renatured by dilution in folding buffer (100 mM Tris/HCl pH 9.5; 1 M L-arginine; 5 mM GSH; 0.5 mM GSSG; 5 mM EDTA). The folding was preformed at a protein concentration of 50 The renaturation sample was incubated for 3 h at 10° C.

d) Purification by Means of Ion Exchange Chromatography

The renatured material was dialyzed against 10 l of 50 mM Na-phosphate pH 7.0; 1 mM EDTA (IEX buffer A) and centrifuged for 30 min at 20,000 rpm. The supernatant was loaded onto a Poros 20 HS column and eluted using a salt gradient (IEX buffer B: 50 mM Na-phosphate pH 7.0, 1 M NaCl, 1 mM EDTA). The protein eluted at 980 mM NaCl (FIG. 3). Non-native rh proNGF can only be removed from the column using denaturing conditions.

EXAMPLE 4

Characterization of rh proNGF a) Determining the Concentration and the Molecular Weight by Means of UV Spectrophotometry To determine the concentration of rh proNGF in the purified samples, an UV spectrum from 240 to 340 nm was taken of the samples dialyzed against 50 mM Na-phosphate pH 7.0, 1 mM EDTA (FIG. 5; the spectrum was obtained using a Beckman DU 640 spectrophotometer). The rh proNGF concentration in the sample was determined by means of absorption at 280 nm. The evaluation was based on a theoretical molar extinction coefficient of 25,680 l/(mol×cm) (calculated according to Gill, S. C., et al., Anal. Biochem. 182 (1989) 319) and a molecular weight of 24,869 Da per monomer (calculated by means of the ExPASy program "pI/Mw" and corrected for three disulfide bonds). The values obtained using the spectrum were in close correlation to the concentrations determined by means of the Bradford method. Molecular weight determination was done using electron spray mass spectrometry. The theoretical mass of recombinant proNGF is 24,869 Da. Experimentally determined were 24,871 Da.

b) Analysis of the Purity and Determination of the Molecular Weight Using SDS Polyacrylamide Gel Electrophoresis 15% polyacrylamide gels were used. Each sample contained 1% (v/v) 2-mercaptoethanol. In the SDS gel, the recombinant human proNGF shows a slightly higher apparent molecular weight than expected: approx. 30 kDa (instead of 24.8 kDa) (FIG. 2).

c) Analysis of the Purity by Means of IEX-HPLC

24 μg (50 μl of a sample containing 0.48 mg/ml rh proNGF) of protein were loaded onto a Poros 20 HS column (125×4 mm) equilibrated with 50 mM Na-phosphate pH 7.0; 1 mM EDTA, and were eluted at a flow rate of 5 ml/min with a linear gradient of 0 to 100% B (B=50 mM Na-phosphate pH 7.0; 2 M NaCl; 1 mM EDTA) in a period of 10 minutes (FIG. 6). The absorption at 280 nm was used for detection (Gyncotek HPLC system with analysis software Chromeleon version 3.14).

d) Analysis of the Purity Using RP C4 HPLC 3.1 μg of rh proNGF (15 μl rh proNGF in a concentration of 0.21 mg/ml) were loaded onto a Poros 10 R1 column (100 mm×4 mm; Perseptive Biosystems) equilibrated with 0.13% TFA. The protein was eluted at a flow rate of 0.8 ml/min with a nonlinear gradient (0-4 min: 6% B; 4-9 min: 6-30% B; 9-24 min: 30-69% B; 24-25 min: 69-100% B; 25-30 min: 100% B)) in a period of 33 minutes. As the eluent B there was used 0.1% (v/v) TFA in 80% (v/v) acetonitrile. The absorption at 220 nm was used for detection (Beckman "Gold" HPLC system with analysis software "Gold V 8.10"). Native rh proNGF eluted in a single peak at a retention time of 14.28 min (FIG. 7).

e) Analysis of the N Terminal Sequence

For N terminal sequence analysis the solubilized IBs were used which had been roughly purified by means of RP HPLC. The N terminal sequence was determined using an Applied Biosystems 476A protein sequencing device. The following amino acid sequence was obtained:

(SEQ ID NO: 7)
H$_2$N-Met-Glu-Pro-His-Ser-Glu-Ser-Asn-Val f) Biological Activity of the Recombinant Human proNGF The physiological activity of rh proNGF was determined using the DRG assay (=dorsal root ganglion assay) (Levi-Montalcini, R., et al., Cancer Res. 14 (1954) 49; Varon, S., et al., Meth. in Neurochemistry 3 (9172) 203). In this assay the stimulation and survival of sensory neurons from dissociated dorsal root ganglia of 7-8 day old chick embryos is determined by means of neurite formation. The rh proNGF sample was adjusted to concentrations of 0.019 to 20.00 ng/ml using culture medium. Per test sample 15,000 neurons were employed. After incubation for 48 hours at 37° C. the number of surviving cells was determined. A solution of rh β-NGF of known concentration was used as the reference sample. The quantitative evaluation is based on the so-called $EC_{50}$ value, i.e. the concentration of NGF promoting the survival of half of the neurons. For rh proNGF an $EC_{50}$ value of 0.369 ng/ml was obtained. In comparison, the $EC_{50}$ value obtained for the rh β-NGF standard was 0.106 ng/ml. Considering the different molecular weight of rh β-NGF and rh proNGF, the biological activity of mature rh β-NGF is about twice as high as that of rh proNGF.

EXAMPLE 5

Preparation of Biologically Active Mature Rh β-NGF by Limited Proteolysis of rh proNGF Human proNGF contains an arginine residue as the last amino acid of the prosequence. Therefore, from this precursor the mature rh β-NGF may be obtained in vitro by limited proteolysis using proteases of suitable substrate specificity such as trypsin.

500 μl of purified rh proNGF were dialyzed against 50 mM Tris/HCl pH 8.0. Following dialysis, a protein concentration of 0.49 mg/ml was measured by running the UV spectrum. Per digestion sample, 20 μg of proNGF were employed. After proteolysis, 3 μg (corresponding to 6 μl) of this sample were analyzed by means of SDS PAGE. As the trypsin stock solution 0.1 μg/ml or 0.01 μg/ml, respectively, were used. The concentration of soy bean trypsin inhibitor (STI) was 1 mg/ml. Both proteins were provided in the form of lyophilized powders (manufacturer: Boehringer Mannheim and Sigma, respectively) and were dissolved in the above-mentioned buffer.

Different mass ratios of trypsin/rh proNGF were used in the limited proteolysis (see Table 3). After an incubation for thirty minutes on ice each reaction was stopped by 5 μg STI.

For control purposes rh proNGF without added protease was also incubated on ice, followed by addition of STI.

TABLE 3

| Ratio trypsin:rh proNGF | M (trypsin) [µg] | V (trypsin) [µl] | V (rh proNGF) [µl] | V (STI) [µl] |
|---|---|---|---|---|
| 1:40 | 0.5 | 5 (0.1 µg/ml) | 40 | 5 |
| 1:100 | 0.2 | 2 (0.1 µg/ml) | 40 | 5 |
| 1:250 | 0.08 | 0.8 (0.1 µg/ml) | 40 | 5 |
| 1:500 | 0.04 | 4 (0.01 µg/ml) | 40 | 5 |
| 1:1000 | 0.02 | 2 (0.01 µg/ml) | 40 | 5 |
| 1:2000 | 0.01 | 1 (0.01 µg/ml) | 40 | 5 |
| 1:2500 | 0.008 | 0.8 (0.01 µg/ml) | 40 | 5 |
| Control | — | — | 20 | 2.5 | g) Analysis of the Cleavage Products by N Terminal Sequencing

The digestion samples with a mass ratio of trypsin:rh proNGF of a) 1:40; b) 1:100, and c) 1:250 were subjected to a more detailed analysis by N terminal sequencing. A band at 13 kDa contained several species (FIG. 8):
N terminus 1: Met$^{-104}$ . . . ;
N terminus 2: Val$^{-35}$ . . . ;
N terminus 3: Ser$^1$ . . . (mature rh β-NGF);
N terminus 4: Gly$^{10}$ . . . ;

These peptides were present in the different samples in differing amounts.

Sample a): N terminus 2: N terminus 3: N terminus 4=4:5:2.

Sample b): N terminus 2: N terminus 3=1:1; N terminus 4 in trace amounts.

Sample c) was analyzed in addition by means of RP C3 HPLC (column: Nucleosil 500-5 C3-PPN; 125 mm×4 mm). Two peaks were obtained: peak 1 (12.32 min): N terminus 1; peak 2 (14.88 min): N terminus 2 and N terminus 3 in a ratio of 2:3.

To obtain mature rh β-NGF from rh proNGF on a preparative scale 1.3 mg of rh proNGF (in 50 mM Tris/HCl pH 8.0; concentration 0.46 mg/ml) were added with trypsin in a mass ratio of 1:250 (trypsin:rh proNGF). The sample was incubated for 30 min on ice. Afterwards, the protease was inactivated by a 40 fold excess based on the mass of soy bean trypsin inhibitor. The cleavage sample was dialyzed against 50 mM sodium phosphate pH 7.0, 1 mM EDTA and then applied to a cation exchange column (1.7 ml Poros 20 HS; Perseptive Biosystems). In a linear salt gradient of 0 to 2 M NaCl the cleavage product eluted in a single peak. The elution at a salt concentration of about 840 mM NaCl corresponded to that of mature rh β-NGF in a control experiment. The yield of purified cleavage product was 17%.

The biological activity of the purified cleavage product was tested by means of the DRG assay. It corresponded to the activity of mature rh β-NGF (Table 4).

TABLE 4

| Species | EC$_{50}$ value [pg/ml] |
|---|---|
| rh β-NGF | 110 |
| rh β-NGF prepared by limited proteolysis of rh proNGF | 171 |

REFERENCES

Barnett, J., et al., J. Neurochem. 57 (1991) 1052
Bradford, M. M., Anal. Biochem. 72 (1976) 248
EP-A 0 544 293
Hefti, F. J., J. Neurobiol. 25 (1994) 1418
Hill, S. C. et al., Anal. Biochem. 182 (1989) 319
Laemmli, U. K., Nature 227 (1970) 680
Levi-Montalcini, R. et al., Cancer Res. 14 (1954) 49
Levi-Montalcini, R., Science 237 (1987) 1154
Marston, F. A., Biochem. J. 240 (1986) 1
Nesterenko, M. V. et al., J. Biochem. Biophys. Methods 28 (1994) 239
Rudolph. R. et al. (1997): Folding Proteins. In: Creighton, T. E. (ed.): Protein function: A Practical Approach, pp. 57-99
Schmelzer, C. H. et al., J. Neurochem. 59 (1992) 1675
Studier, F. W. et al., J. Mol. Biol. 189 (1986) 113
Suter, U. et al., EMBO J. 10 (1991) 2395
SWISS-PROT Protein Sequence Database No. P01138
Thoenen, H. et al., Physiol. Rev. 60 (1980) 1284
Ullrich, A. et al., Nature 303 (1983) 821
U.S. Pat. No. 5,235,043
U.S. Pat. No. 5,593,856
U.S. Pat. No. 5,606,031
U.S. Pat. No. 5,683,894
Varon, S. et al., Meth. in Neurochemistry 3 (1972) 203
WO 97/47735
Yankner, B. A. et al., Annu. Rev. Biochem. 51 (1982) 845

What is claimed is:

1. A method for the preparation of biologically active proNGF, comprising:
   (a) recombinantly expressing a proNGF coding sequence in a prokaryote to produce a proNGF polypeptide comprising its complete prosequence, wherein the proNGF polypeptide comprising its complete prosequence is present in the prokaryote in inclusion bodies;
   (b) transferring the inclusion bodies comprising the proNGF polypeptide comprising its complete prosequence into a solution of a denaturing agent to obtain a denatured and solubilized proNGF polypeptide; and
   (c) transferring the denatured and solubilized proNGF polypeptide into a non-denaturing or weakly denaturing renaturation solution with a pH of between 7 and 10, wherein the denatured and solubilized proNGF polypeptide remains soluble in the renaturation solution and assumes a biologically active conformation comprising the same disulfide bonds that are present in native proNGF,
   whereby biologically active proNGF is obtained.

2. The method of claim 1, wherein the renaturation solution contains arginine.

3. The method of claim 2, wherein the concentration of arginine is 0.2 to 1.5 mol/l.

4. The method of claim 2, wherein the renaturation solution comprises a thiol component in its reduced and oxidized form.

5. The method of claim 3, wherein the renaturation solution comprises a thiol component in its reduced and oxidized form.

6. The method of claim 2, wherein guanidinium hydrochloride or urea is used as the denaturing agent.

7. The method of claim 3, wherein guanidinium hydrochloride or urea is used as the denaturing agent.

8. The method of claim 1, wherein the renaturation solution comprises a thiol component in its reduced and oxidized form.

9. The method of claim 8, wherein guanidinium hydrochloride or urea is used as the denaturing agent.

10. The method of claim 1, wherein guanidinium hydrochloride or urea is used as the denaturing agent.

11. The method of claim 1, further comprising isolating the biologically active proNGF.

12. A method for the preparation of biologically active β-NGF polypeptide, comprising:
    (a) recombinantly expressing a proNGF coding sequence in a prokaryote to produce a proNGF polypeptide comprising its complete prosequence, wherein the proNGF polypeptide comprising its complete prosequence is present in the prokaryote in inclusion bodies;
    (b) transferring the inclusion bodies comprising the proNGF polypeptide into a solution of a denaturing agent to obtain a denatured and solubilized proNGF polypeptide;
    (c) transferring the denatured and solubilized proNGF polypeptide into a non-denaturing or weakly denaturing renaturation buffer with a pH of between 7 and 10, wherein the proNGF polypeptide remains soluble in the renaturation buffer and assumes a biologically active conformation with the same disulfide bonds present as in native proNGF; and
    (d) cleaving off the prosequence,
    whereby a biologically active β-NGF polypeptide is prepared.

13. The method of claim 12, further comprising isolating the biologically active β-NGF polypeptide.

14. The method of claim 12, wherein the cleaving step comprises employing a protease with a substrate specificity for cleaving after the amino acid arginine.

15. The method of claim 14, wherein the protease is trypsin.

16. The method of claim 12, wherein the denaturing agent comprises guanidinium hydrochloride or urea.

17. The method of claim 12, further comprising isolating the biologically active β-NGF.

* * * * *

UNITED STATES PATENT AND TRADEMARK OFFICE

(12)          CERTIFICATE EXTENDING PATENT TERM
UNDER 35 U.S.C. § 156

| | | | |
|---|---|---|---|
| (68) | PATENT NO. | : | 8,501,439 |
| (45) | ISSUED | : | August 6, 2013 |
| (75) | INVENTOR | : | Rattenholl et al. |
| (73) | PATENT OWNER | : | Dompé farmaceutici S.p.A. |
| (95) | PRODUCT | : | OXERVATE® (cenegermin-bkbj) |

This is to certify that an application under 35 U.S.C. § 156 has been filed in the United States Patent and Trademark Office, requesting extension of the term of U.S. Patent No. 8,501,439 based upon the regulatory review of the product OXERVATE® (cenegermin-bkbj) by the Food and Drug Administration. According to United States Patent and Trademark Office records, the original expiration date of the patent as of the date of issuance of this certificate is June 23, 2020. Because it appears that the requirements of the law have been met, this certificate extends the term of the patent for the period of

(94)                              864 days subject to the payment of maintenance fees as provided by law, with all rights pertaining thereto as provided by 35 U.S.C. § 156.

I have caused the seal of the United States Patent and Trademark Office to be affixed this <u>5th day</u> of <u>May 2021</u>.

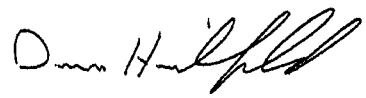

Drew Hirshfeld
Commissioner for Patents, Performing the Functions and Duties of the Under Secretary of Commerce for Intellectual Property and Director of the United States Patent and Trademark Office